United States Patent
Jensen et al.

(10) Patent No.: US 6,814,489 B2
(45) Date of Patent: Nov. 9, 2004

(54) 3D RECONSTRUCTION SYSTEM AND METHOD UTILIZING A VARIABLE X-RAY SOURCE TO IMAGE DISTANCE

(75) Inventors: Vernon Thomas Jensen, Draper, UT (US); Francois Emmanuel Falco, Draper, UT (US); Barry Frederick Belanger, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 166 days.

(21) Appl. No.: 10/064,160

(22) Filed: Jun. 17, 2002

(65) Prior Publication Data

US 2003/0099328 A1 May 29, 2003

Related U.S. Application Data (60) Provisional application No. 60/332,516, filed on Nov. 23, 2001.

(51) Int. Cl.[7] .................................................. H05G 1/02
(52) U.S. Cl. .......................................... 378/197; 378/62
(58) Field of Search ................................ 378/198, 195, 378/205, 206, 207, 197, 13, 62, 4

(56) References Cited

U.S. PATENT DOCUMENTS

| | | | |
|---|---|---|---|
| 4,501,011 A | | 2/1985 | Hauck et al. |
| 5,095,501 A | * | 3/1992 | Kobayashi ................... 378/196 |
| 5,287,546 A | | 2/1994 | Tesic et al. |
| 5,319,205 A | | 6/1994 | Kline et al. |
| 5,338,936 A | | 8/1994 | Gullberg et al. |
| 5,375,156 A | * | 12/1994 | Kuo-Petravic et al. ......... 378/9 |
| 5,627,873 A | | 5/1997 | Hanover et al. |
| 5,642,395 A | | 6/1997 | Anderton et al. |
| 5,654,997 A | | 8/1997 | Brownell et al. |
| 6,048,097 A | | 4/2000 | Heinzi |
| 6,050,724 A | * | 4/2000 | Schmitz et al. .............. 378/205 |
| 6,325,537 B1 | * | 12/2001 | Watanabe .................... 378/197 |
| 6,412,978 B1 | * | 7/2002 | Watanabe et al. ........... 378/197 |
| 6,428,206 B1 | * | 8/2002 | Watanabe .................... 378/197 |
| 6,480,574 B2 | * | 11/2002 | Goto ........................... 378/154 |
| 6,508,586 B2 | * | 1/2003 | Oota ........................... 378/196 |

FOREIGN PATENT DOCUMENTS

EP            1016375 A1      5/2000

* cited by examiner

*Primary Examiner*—Edward J. Glick
*Assistant Examiner*—Hoon Song
(74) *Attorney, Agent, or Firm*—McAndrews, Held & Malloy, Ltd.; Peter J. Vogel; Michael A. Dellapenna (57) ABSTRACT

A medical imaging system comprises a C-arm unit having an x-ray source for generating x-rays and a receptor for obtaining image exposures from received x-rays. The C-arm unit moves the x-ray source and receptor along an image acquisition path between at least first and second exposure positions. The C-arm unit rotates about a central axis. Source and receptor brackets mount the x-ray source and receptor, respectively, to the C-arm unit. The source and receptor brackets move at least one of the x-ray source and receptor in a radial direction toward and away from the central axis of the C-arm unit to maintain a desired distance between the patient and the x-ray source and receptor. An image processor collects a series of image exposures from the receptor and constructs a three dimensional volumetric data set which is displayed on a display.

31 Claims, 5 Drawing Sheets

3D RECONSTRUCTION SYSTEM AND METHOD UTILIZING A VARIABLE X-RAY SOURCE TO IMAGE DISTANCE

CROSS REFERENCE TO RELATED APPLICATIONS

This application is related to, and claims priority from, Provisional Application No. 60/332,516 filed Nov. 23, 2001 titled "3D Reconstruction System and Method Utilizing a Variable X-ray Source to Image Distance", the complete subject matter of which is incorporated herein by reference in its entirety.

BACKGROUND OF INVENTION

Certain embodiments of the present invention generally relate to an x-ray system capable of varying the distance between the image receptor and the x-ray source. Certain embodiments of the present invention generally relate to a mobile C-arm based x-ray system that varies the source to image distance while acquiring images for three dimensional (3D) image reconstruction.

3D x-ray imaging has become increasingly useful in medical diagnostic procedures and surgical planning. Computerized Tomography (CT) was the first type of system used for these purposes. Conventional CT systems employ a fan-shaped x-ray beam directed at a detector array which has a width dimension much smaller than its length. To obtain complete scans of a significant volume of anatomy, the x-ray tube and detector array are rotated around the patient a number of times while the patient is advanced along the axis of rotation.

More recently, area-beam detectors, such as image intensifiers, have been employed in acquiring 3D image data. Such systems are based on conventional x-ray systems used for cardiovascular and/or surgical interventional imaging. The advantage to such systems is that they can acquire a full 3D dataset faster than a CT system, and thereby better capture dynamic events. For example, area-beam 3D imaging of the vessels of the brain using contrast agents has become extremely in the diagnosis and treatment of intracranial aneurysms.

Heretofore, area-beam detector 3D x-ray imaging systems have operated by rotating an x-ray tube and detector in circular paths around a central axis of rotation. The axis of rotation is positioned to be at the center of the region or volume of interest of the patient anatomy. The x-ray source and x-ray receptor, usually an image intensifier, are typically mounted on opposite ends of a rotating C-arm support assembly. The x-ray source irradiates a patient with x-rays that impinge upon a region of interest (ROI) and are attenuated by internal anatomy. The attenuated x-rays emerge from a back-side of the patient and are incident upon the receptor. 3D image data is acquired by taking a series of images as the x-ray tube/C-arm/receptor assembly is rotated about the axis of rotation on which the region of interest within the patient is centered.

Conventional mobile C-arm assemblies utilize simple support structures and geometries to mount the x-ray source and the receptor on the C-arm. The support structure holds the x-ray source and receptor on the C-arm and maintains a predetermined, constant distance between the x-ray source and receptor. Hence, the distance between the x-ray source and the axis of rotation, and the distance between the receptor and the axis of rotation remain constant and fixed.

However, conventional mobile C-arm assemblies experience certain problems when using an x-ray source and receptor fixedly mounted on a C-arm to generate 3D reconstruction images. The 3D reconstruction images are formed for an ROI located within a patient having an oblong cross-section (e.g., a patient laying face up on a table may have a longer width from shoulder to shoulder and a shorter height from front to back).

FIGS. 4–7 illustrate a conventional C-arm assembly 300 that rotates about a circular path 312. The radius of the circular path 312 must be large enough to pass the widest portion of the patient's anatomy (e.g., shoulder to shoulder). Hence, during a set-up operation before acquiring a series of patient images, the patient is positioned between the image receptor 306 and x-ray source 304 to prevent the x-ray source 304 or image receptor 306 from contacting the patient during any part of the rotational scan. In order to obtain patient images, the x-ray source 304 and image receptor 306 are rotated to various scan angles about the patient. Each scan angle has a corresponding trajectory through the ROI. As the scan angle varies, the trajectory between the image receptor 306 and x-ray source 304 similarly varies and, in addition, the distance between the image receptor 306 and the exit surface of the patient 308 varies considerably. The distance also varies between the x-ray source 304 and entrance surface of the patient 309.

Figure 4:
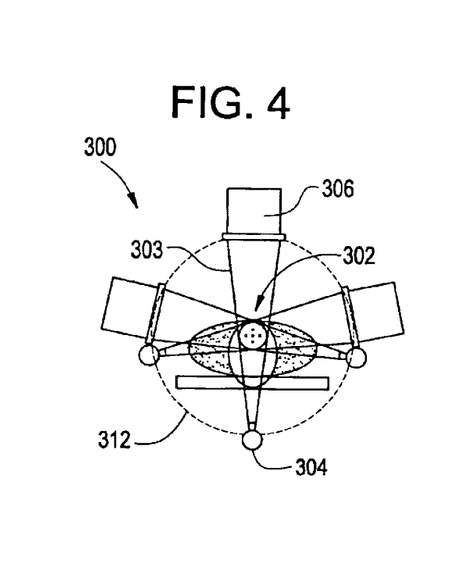
FIG. 4 illustrates a graphical representation of a range of motion of a conventional x-ray system.
Figure 5:
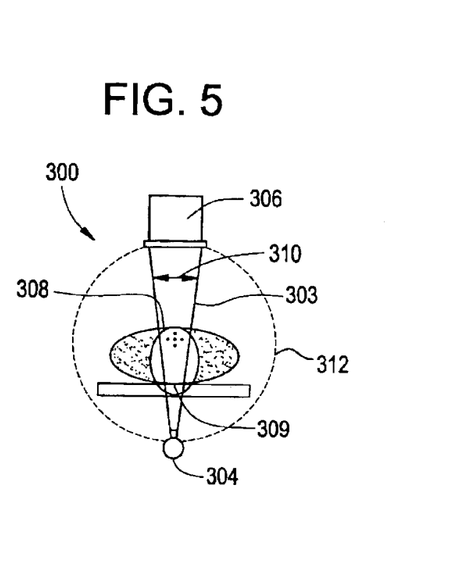
FIG. 5 illustrates a graphical representation of a range of motion of a conventional x-ray system.

As shown in FIGS. 4 and 5, the foregoing phenomenon result in a conventional C-arm assembly 300 affording a limited 3D reconstruction volume 302. The C-arm assembly 300 operates in an ISO centered manner in which the ROI within the patient remains centered within the x-ray field 303. In order to maintain the ROI centered within the x-ray field 303, the x-ray source 304 and image receptor 306 rotate about the patient along a circular arc 312. The patient is oblong shaped and thus as the x-ray source 304 and image receptor 306 rotate about a circular path, the image receptor 306 rotates from positions proximate the patient to positions remote from the patient. When the image receptor 306 is located remote from the patient exit surface 308, the area of anatomy that can be imaged is limited by the geometric magnification (generally denoted by the arrow 310). Therefore, the dimensions of reconstruction volume 302 are limited as well.

Figure 6:
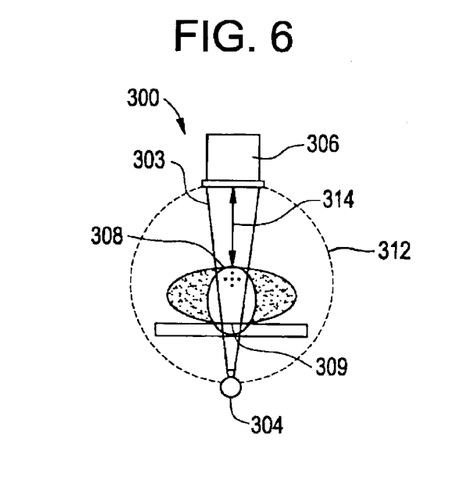
FIG. 6 illustrates a graphical representation of a range of motion of a conventional x-ray system.

Also, as shown in FIG. 6, the image receptor 306 is positioned a distance 314 from the patient exit surface 308. The x-rays are emitted from the x-ray source 304 in a cone beam shape and thus as the image receptor 306 is moved further from the patient, the x-ray field 303 expands. Expansion of the x-ray field 303 effectively magnifies at the image receptor 306 each image obtained from the region of interest. As the distance 314 increases, the amount of magnification greatly increases, particularly for images taken at scan angles associated with the shortest distance through the anatomy (e.g., front to back in the example of FIGS. 4–7). The large amount of magnification associated with positioning the image receptor 306 a distance 314 remote from the patient exit surface 308 causes the image to be blurred, due to the large projected penumbra of the focal spot. As the sharpness of the focal spot decreases, the quality of the 2D image data decreases, and therefore the quality of the 3D reconstructed data decreases.

Figure 7:
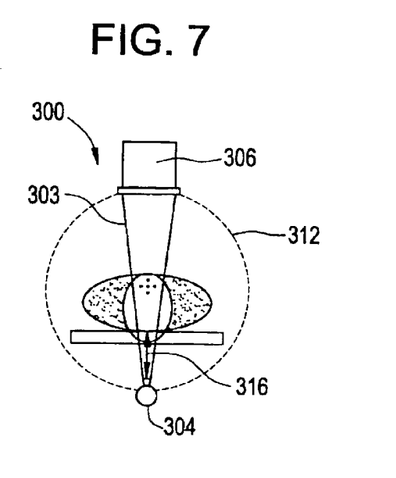
FIG. 7 illustrates a graphical representation of a range of motion of a conventional x-ray system.

Further, as shown in FIG. 7, the distance from the x-ray source 304 to the image receptor 306 remains constant. However, as the distance 316 decreases, the image receptor 306 is positioned farther away from the patient in some views, while the x-ray source 304 is positioned closer to the patient's skin than necessary at certain scan angles, giving rise to unnecessarily high irradiation doses.

Hence, a need remains for an improved x-ray imaging system capable of reconstructing 3D volumes of patient information for a region of interest that overcomes the problems above and previously experienced.

SUMMARY OF INVENTION

In accordance with at least one embodiment, a medical diagnostic imaging system is provided. The system has a C-arm unit that moves an image receptor and x-ray source around a patient in non-circular arcs. The receptor and x-ray source are supported by a support structure, and at least one of the receptor and x-ray source are moveable upon the support structure, such as in a radial direction toward and away from a central axis of the support structure. The distances between at least one of the patient and source, and the patient and receptor are varied such that the receptor and/or source remain positioned within a desired distance from the patient's surface.

In accordance with at least one embodiment, the medical diagnostic imaging system includes an image processor. The image processor collects image exposures at exposure positions as the receptor and x-ray source are moved around the patient. Position data corresponding to the exposure positions is collected and used, together with the image exposures, to construct a three dimensional volumetric data set. Images are displayed based upon the three dimensional volumetric data set.

BRIEF DESCRIPTION OF DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION

Figure 1:
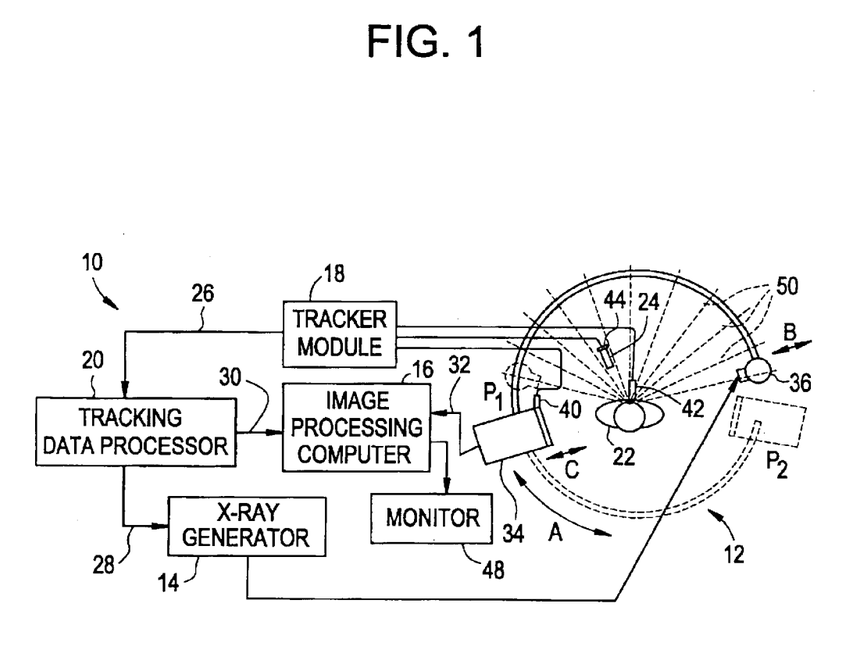
FIG. 1 illustrates a block diagram of an x-ray imaging system formed in accordance with an embodiment of the present invention.

FIG. 1 illustrates an x-ray imaging system 10 that includes a C-arm 12 that is electrically connected to an x-ray generator 14, an image processing computer 16 and a tracker module 18. The tracker module 18 communicates with a tracking data processor 20 which in turn communicates with the image processing computer 16 and x-ray generator 14. The image processing computer 16 communicates with a monitor 48.

The C-arm 12 includes an x-ray source 36 movably mounted to one side and an x-ray receptor device 34 movably mounted to the opposed side. The x-ray receptor device 34 may be a flat panel detector, image intensifier and the like. The C-arm 12 is movable in several directions along multiple image acquisition paths, including, among others, an orbital tracking direction, longitudinal tracking direction, lateral tracking direction, transverse tracking direction, pivotal tracking direction, and "wig-wag" tracking direction. The orbital rotation direction is denoted by arrow A. FIG. 1 illustrates the C-arm 12, x-ray receptor device 34 and x-ray source 36 in solid lines while located at a first position (P1), and in shadow lines while located at a second position (P2). Alternatively, the C-arm 12, x-ray receptor device 34 and x-ray source 36 may be moved along image acquisition paths in the longitudinal, lateral, transverse and wig-wag tracking directions and the like. The x-ray source 36 and x-ray receptor device 34 are movable in radial directions denoted by arrows B and C, respectively.

The tracker module 18 monitors the position of the patient 22, the x-ray receptor device 34, and an instrument or tool 24 (if present) used by a doctor during a diagnostic or interventional surgical procedure with sensors 40–44. The tracker module 18 provides tracking component coordinates 26 with respect to each of the patient 22, x-ray receptor device 34, and instrument 24 to the tracking data processor 20. The tracking data processor 20 uses the tracking component coordinates 26 to continuously calculate the positions of the x-ray receptor device 34, patient 22 and instrument 24 with respect to a coordinate system defined relative to a coordinate system reference point or central axis. The reference point for the coordinate system is dependent, in part, upon the type of tracker module 18 to be used. The tracking data processor 20 sends control or trigger commands 28 to the x-ray generator 14 which in turn causes one or more exposures to be taken by the x-ray source 36 and x-ray receptor device 34. The tracking data processor 20 provides exposure reference data 30 to the image processing computer 16. The control or trigger commands 28 and exposure reference data 30 are generated by the tracking data processor 20, as explained in more detail below, based on the tracking component coordinates 26 as the C-arm is moved along an image acquisition path.

By way of example, the C-arm 12 may be manually or automatically moved between first and second positions P1 and P2 as a series of exposures are obtained. The image acquisition path may be along the orbital rotation direction and the x-ray receptor device 34 may be rotated through a range of motion from 0 to 145° or from 0 to 190°. Alternatively, the image acquisition path may be along the lateral rotation.

The image processing computer 16 collects a series of image exposures 32 from the receptor 34 as the C-arm 12 is rotated. The x-ray receptor device 34 collects an image exposure 32 each time the x-ray source 36 is triggered by the x-ray generator 14. The image processing computer 16 combines each image exposure 32 with corresponding exposure reference data 30 and uses the exposure reference data 30 to construct a three-dimensional volumetric data set as explained below in more detail. The three-dimensional volumetric data set is used to generate images, such as slices, of a region of interest from the patient. For instance, the image processing computer 16 may produce from the volumetric data set saggital, coronal and/or axial views of a patient spine, knee, and the like.

Figure 2:
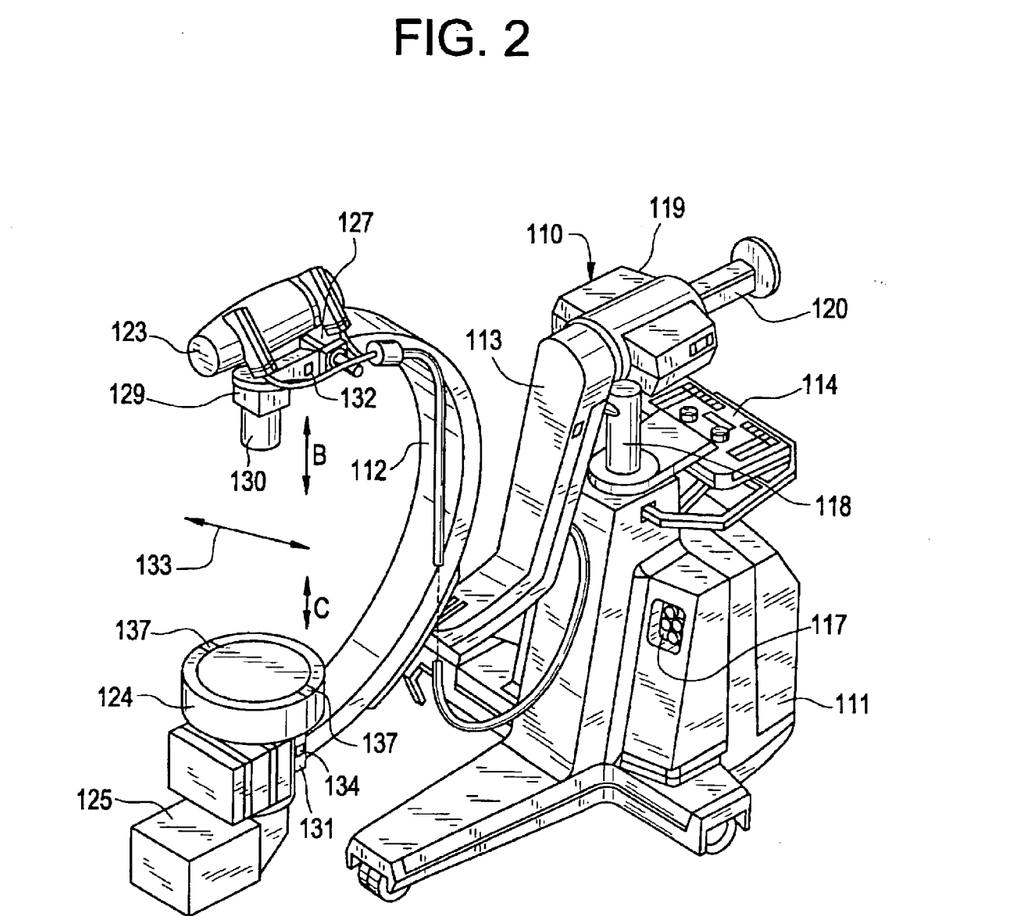
FIG. 2 illustrates a C-arm assembly that may be used in accordance with an embodiment of the present invention.

FIG. 2 illustrates an exemplary mobile C-arm x-ray unit 110 that may operate based on positional information entered by the operator and/or position data received from one or more sensors. The unit 110 is comprised of a mainframe 111, a C-arm 112, an L-arm 113 and control panel 114. The lower portion of the mainframe 111 forms a T-shaped structure, wherein casters are utilized to provide mobility of the unit 110. The mainframe 111 includes a power panel 117 for controlling the coupling of power, as well as other devices, to unit 110. The mainframe 111 also includes a vertical lift column 118 that permits the C-arm 112 and L-arm 113 to move vertically in relation to mainframe 111. Vertical lift column 118 terminates in an upper housing 119, wherein horizontal extension arm 120 passes through upper housing 119 and permits arm 120 to move perpendicularly in relation to vertical lift column 118 by movement of the horizontal extension arm 120 in relation to upper housing 119. The C-arm 112 may be moved along the axis of the horizontal extension arm 120 to effect transverse tracking motion. The L-arm 113 is capable of pivoting (pivotal tracking motion) about the horizontal extension arm 120 such that the L-arm 113 can be made to pivot in a 360° arc. The horizontal extension arm 120 is coupled to one end of the L-arm 113, while the other end of the L-arm 113 is coupled to C-arm 112.

The C-arm 112 is a C-shaped structure having an x-ray emitter 123 at one end of the C-arm 112 and a receptor, such as image receptor 124 with a camera 125, at the other end of the C-arm 112. Alternatively, a flat panel image detector or other x-ray receptor device may be used instead of the image receptor 124 and camera 125. A collimator assembly 129 may be provided for collimating the x-ray beam from the x-ray emitter 123. A spacer 130 provides a safety distance that a patient may be brought within the x-ray emitter 123. Sensors 137 may be located on image receptor 124 to detect the position and/or contour of a patient.

The x-ray emitter 123 is supported within an emitter bracket 127, while the image receptor 124 is supported within a receptor bracket 131. The emitter and receptor brackets 127 and 131 are automatically controlled to move the x-ray emitter 123 and image receptor 124 along radial paths (denoted by arrows B and C, respectively) toward and away from a center axis 133 that extends in a direction perpendicular to a plane containing the x-ray emitter 123 and image receptor 124. The C-arm 112 rotates about the center axis 133. The mainframe 111 includes a CPU which automatically controls the emitter bracket 127 and the receptor bracket 131 to effect radial movement of the x-ray emitter 123 and the image receptor 124, respectively. Optionally, the emitter bracket 127 and the receptor bracket 131 may permit manual movement of the x-ray emitter 123 and the image receptor 124 along the radial paths B and C. The control panel 114 may permit an operator to enter parameters specifying discrete radial positions of the x-ray emitter 123 and image receptor 124 associated with particular scan positions. For instance, the operator may use the control panel 114 to move the C-arm 112 to discrete scan positions and then move the x-ray emitter 123 and the image receptor 124 to corresponding radial positions. Once maximum and minimum radial positions are defined for the x-ray emitter 123 and the image receptor 124, the mainframe 111 may then extrapolate intermediate radial positions, in relation to the center axis 133, to which the x-ray emitter 123 and the image receptor 124 are moved for each discrete scan angle over the range of motion of the C-arm 112.

Optionally, the radial position of the emitter and receptor brackets 127 and 131 may be measured and controlled through sensors 132 and 134 located on the emitter and receptor brackets 127 and 131. Optionally, the emitter and receptor brackets 127 and 131 may include stepper motors having a known reference point corresponding to a known radial relation between the C-arm and the x-ray emitter 123, and the C-arm and the image receptor 124, respectively. The mainframe 111 drives the stepper motors by a desired number of degrees or rotations to move the x-ray emitter 123 and image receptor 124 desired distances toward or away from the central axis 133.

The unit 110 is typically coupled to a monitoring unit wherein such monitoring unit includes equipment necessary for viewing the video image provided by the camera 125. The coupling is accomplished through cables coupled through power panel 117 of the unit 110 to the monitoring equipment, such as a video display monitoring cart, which is typically used in conjunction with C-arm x-ray unit 110. Alternatively, the monitoring equipment and video display monitoring card may be formed integral with the C-arm x-ray unit 110.

Figure 3:
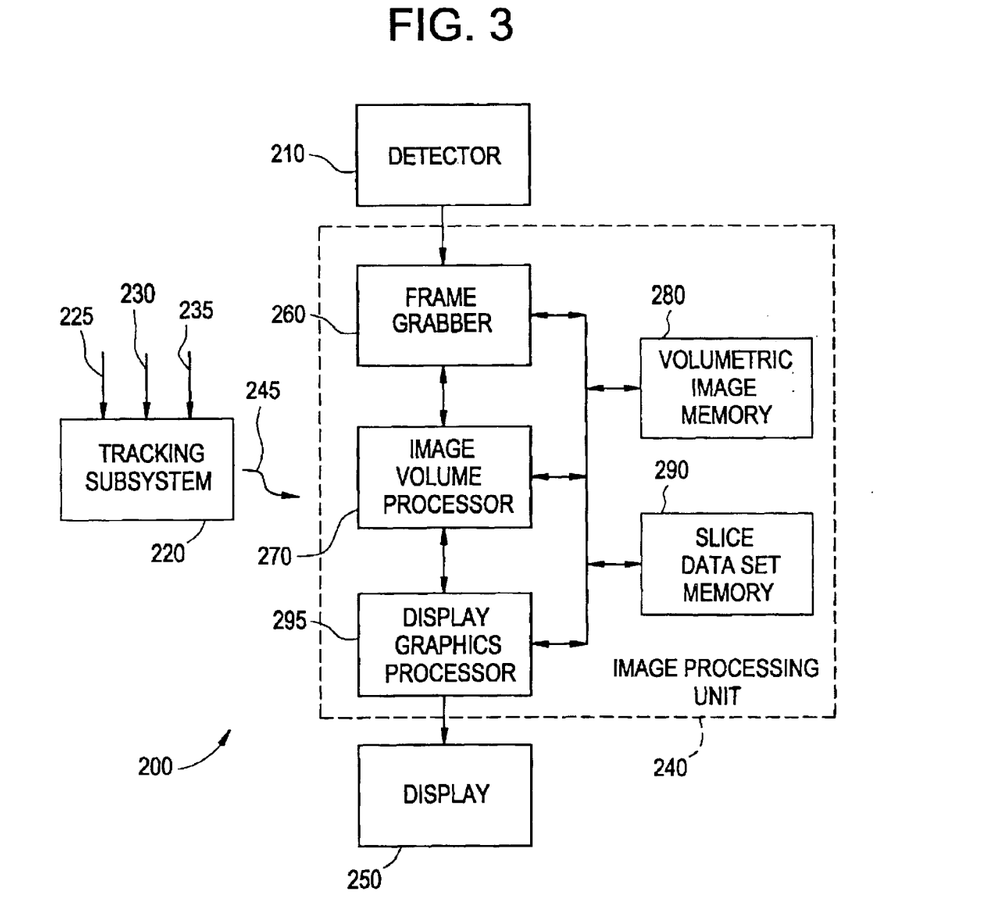
FIG. 3 illustrates a block diagram of an alternative x-ray imaging system formed in accordance with an embodiment of the present invention.

FIG. 3 illustrates an alternative x-ray imaging system. X-ray imaging system 200 includes a detector 210 mounted to a C-arm for detecting x-rays passed through a patient. A tracking subsystem 220 receives patient coordinate information 225, detector coordinate information 230 and instrument coordinate information 235. The tracking subsystem 220 may receive the coordinate information 225–235 from a tracker module, such as from tracker module 18 in FIG. 1 or from a mainframe, such as mainframe 111 in FIG. 2. The coordinate information 225–235 generated by the tracker module 18 is based on real time measurements of the positions of the detector 210, an instrument 24 (if used) and the patient 22. The coordinate information 225–235 generated by the mainframe 111 is based on measurements of the position of the C-arm assembly of FIG. 2, measurements of the radial positions of the x-ray emitter 123 and image receptor 124, and previously entered radial positions of the x-ray emitter 123 and image receptor 124. The radial position of the x-ray emitter 123 and image receptor 124 may be obtained from sensors 132 and 134 located on, or from stepper motors used to drive radial movement of, the emitter bracket 127 and receptor bracket 131. The tracking subsystem 220 processes the coordinate information 225–235 and passes it to an image processing unit 240 which receives exposure frames from the detector 210 and outputs image frames to the display 250. The image processing unit 240 includes a frame grabber 260 which collects exposure frames from the detector 210 at points in time dictated by the position data 245 provided from the tracking subsystem 220.

The exposure frames are passed from the frame grabber 260 to the image volume processor 270 which manages storage of exposure frames in a volumetric image memory 280. The image volume processor 270 constructs a three-dimensional patient data volume in the volumetric image memory 280. The 3-D patient data volume may be constructed based upon very few exposure frames, such as 10 and the like. As additional exposure frames are obtained by the frame grabber 260, the accuracy and completeness of the 3-D patient data volume is improved. In addition to constructing the 3-D patient data volume, the image volume processor 270 also constructs image slices from the volume. The slices are stored in the slice data set memory 290.

The display graphics processor 295 accesses the slice data set memory 290 to display the image slices on the display 250. The display graphics processor 295 also constructs graphical representations of the instrument or tool 24 and overlays the instrument graphic with the image slices on the display 250. The display graphics processor 295 may present multiple two-dimensional image slices simultaneously on the display 250 with instrument graphics superimposed upon each image slice. Alternatively or in combination with image slices, the display graphics processor 295 may construct a three-dimensional rendering of the 3-D patient data volume and display the three-dimensional rendering on the display 250 separately or in combination with a three-dimensional graphical representation of the instrument 24. The three-dimensional patient image and three-dimensional instrument graphic may be controlled to rotate (in a videotype format) to permit viewing of the patient data volume from multiple angles and to permit viewing of the instrument graphic from multiple angles. Rotation of the three-dimensionally displayed patient data volume may be automatic, such as in a simulated video format, or may be controlled manually in a stepwise manner by the operator of the system. For example, the operator may rotate the image (s) by clicking on the region of interest with a mouse and dragging the image to cause rotation and/or translation.

Optionally, the C-arm assembly may control radial motion of the x-ray emitter 123 and/or image receptor 124 based on "capacitive sensing" for patient contour mapping. For example, sensors 137 may be located on or proximate the imaging plane of the image receptor 124. During a 3D acquisition procedure, as the C-arm assembly is rotated through a scan range, the sensors 137 detect the position and/or contour of the patient surface. The sensors 137 provide the position/contour information as feedback to the mainframe 111. The mainframe 111 uses the position/contour information to drive the receptor bracket 131 and move the image receptor 124 radially in the direction of arrow C. The mainframe 111 drives the receptor bracket 131 in a manner to attempt to retain an imaging plane of the image receptor 124 within a close tolerance, or a predefined distance, of the patient's surface. Similarly, the mainframe 111 drives the emitter bracket 127 and moves the x-ray emitter 123 radially in the direction of arrow B to maintain a uniform distance between the x-ray emitter 123 and the image receptor 124.

For example, the sensors 137 may represent pairs of LED emitters and detectors located on opposite sides of the image receptor 124, with multiple LED emitter/detector pairs spaced different distances from the imaging plane of the image receptor 124. The image receptor 124 may be driven radially toward the patient until an outer LED emitter/receptor pair (e.g., located furthest from the imaging plane) is broken by the patient's surface, but an inner LED emitter/receptor pair (e.g., located closest to the imaging plane) remains unbroken. Once the outer LED emitter/receptor pair is broken, the receptor bracket 131 is stopped. The x-ray emitter 123 may then be driven radially away from the patient until a desired distance between the x-ray emitter 123 and image receptor 124 is obtained. Optionally, x-ray emitter 123 may be driven radially away from the patient simultaneously as the image receptor 124 is driven towards the patient. Once the image receptor 124 and x-ray emitter 123 are in position, a patient image is obtained.

After the patient image is obtained, the C-arm is moved to the next angular scan position and the image receptor 124 is moved radially toward or away from the patient. By way of example only, as the C-arm is moved from an angular position proximate a patient's side to an angular position above the patient's chest, the image receptor 124 becomes positioned further from the patient's surface. Hence, the patient's surface no longer interrupts the sensors 137, or outer LED emitter/receptor pair. The sensors 137 feed this information to the mainframe 111 which in turn drives the receptor bracket 131 to move the image receptor 124 radially inward toward the patient's chest. The image receptor 124 is moved inward until the outer LED emitter/receptor pair is again broken by the patient's surface.

Optionally, the sensors 137 (FIG. 2) may be electromagnetic, ultrasound or otherwise. Electromagnetic sensors continuously detect the absolute distance between the image receptor 124 and the patient. Optionally, sensors 137 may be used to detect and control the position of the x-ray emitter 123 relative to the patient.

Figure 8:
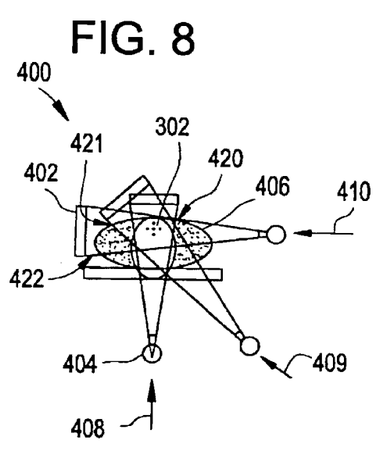
FIG. 8 illustrates a graphical representation of a range of motion of an x-ray imaging system formed in accordance with an embodiment of the present invention.
Figure 9:
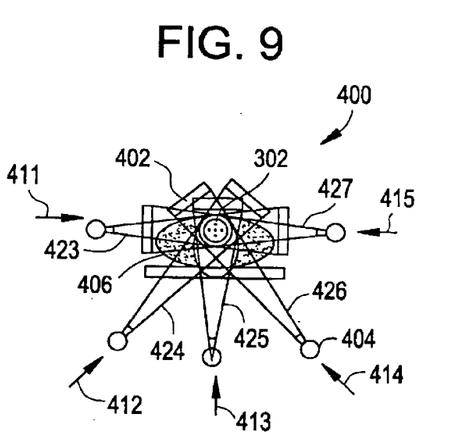
FIG. 9 illustrates a graphical representation of a range of motion of an x-ray imaging system formed in accordance with an embodiment of the present invention.
Figure 10:
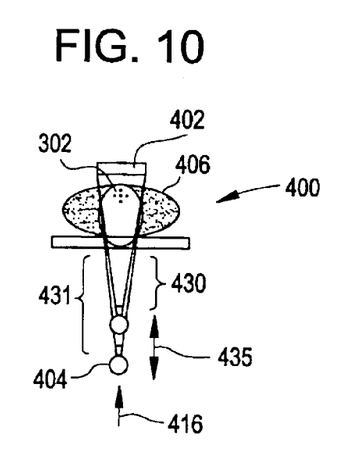
FIG. 10 illustrates a graphical representation of a range of motion of an x-ray imaging system formed in accordance with an embodiment of the present invention.

FIGS. 8–10 illustrate an x-ray assembly 400 at different scan angles 408–416 and with the image receptor 402 and x-ray source 404 moved to different radial distances 420–431 from the patient 406. As shown in FIG. 8, the x-ray assembly 400 when initially located at scan angle 408, the image receptor 402 is spaced a distance 420 from the surface of the patient 406. Once the x-ray assembly 400 is rotated to the scan angle 409, the image receptor 402 is moved radially outward to prevent the image receptor 402 from contacting the patient 406. When at scan angles 409 and 410, the image receptor 402 is located distances 421 and 422, respectively from the patient 406. The x-ray source 404 may also be moved radially to maintain a desired distance between the x-ray source 404 and the image receptor 402.

As shown in FIG. 9, the distance 423–427 is varied between the x-ray source 404 and the patient 406, and the image receptor 402 and the patient 406 when moved between the scan angles 411–415. When the x-ray assembly 400 is at scan angle 411, the x-ray source 404 is located at a radial distance 423 from the patient 406. When the x-ray assembly 400 is rotated to scan angle 412, the image receptor 402 is moved radially inward towards the patient 406, and the x-ray source 404 is moved radially outward to distance 424 in order to maintain the desired distance between the x-ray source 404 and the image receptor 402. When at scan angles 413, 414, and 415, the x-ray source 404 is moved radially to distances 425, 426, and 427, respectively. Alternatively, as shown in FIG. 10, the x-ray source 404 is moved radially in the direction of arrow 435 from a first position located a distance 431 from the patient to a second position located a distance 430 from the patient. Therefore, it should be understood that the x-ray source 404 and the image receptor 402 may be moved independently to increase or decrease the radial distance between the image receptor 402 and the x-ray source 404, and/or the radial distance between the x-ray source 404 or image receptor 402 and the patient 406.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A medical diagnostic imaging system, comprising:
   a C-arm unit having an x-ray source for generating x-rays and a receptor for obtaining image exposures from received x-rays, said C-arm unit moving said x-ray source and receptor along an image acquisition path between at least first and second exposure positions, said C-arm unit rotating about a central axis;

x-ray source and receptor brackets mounting said x-ray source and receptor, respectively, to said C-arm unit, said x-ray source and receptor brackets moving at least one of said x-ray source and receptor in a radial direction toward and away from said central axis of the C-arm unit to maintain a desired distance between said x-ray source and receptor;

an image processor collecting a series of image exposures from said receptor including at least first and second image exposures obtained while said x-ray source and receptor are located at said at least first and second exposure positions, respectively, said image processor collecting position data for multiple exposure positions corresponding to said series of image exposures, said image processor constructing a three dimensional (3D) volumetric data set based on said series of image exposures and said position data for said multiple exposure positions; and a display displaying images based on said 3D volumetric data set.

2. The medical diagnostic imaging system of claim 1, further comprising a mainframe rotating said x-ray source and receptor to a first scan angle and radially moving said x-ray source and receptor to x-ray source and receptor radial distances, respectively, said x-ray source and receptor radial distances being different from one another and corresponding to distances from said central axis to said x-ray source and receptor, respectively.

3. The medical diagnostic imaging system of claim 1, further comprising a control panel for setting maximum and minimum radial distances relative to said central axis for at least one of said receptor and x-ray source.

4. The medical diagnostic imaging system of claim 1, further comprising a tracking subsystem receiving coordinate data comprising at least one of patient, receptor, and instrument coordinate information based on a distance between said central axis and one of a patient, said receptor, and an instrument, respectively, said x-ray source and receptor moving in a radial direction relative to said central axis based on said coordinate data while said x-ray source and receptor are located at said at least first and second exposure positions.

5. The medical diagnostic imaging system of claim 1, said receptor further comprising at least one sensor detecting a radial position of said receptor relative to a patient surface.

6. The medical diagnostic imaging system of claim 1, further comprising a mainframe calculating a plurality of radial distances relative to said central axis for each of said receptor and x-ray source, each radial distance of said plurality of radial distances associated with an image exposure in said series of image exposures.

7. The medical diagnostic imaging system of claim 1, further comprising a mainframe receiving x-ray source position data indicative of a distance between a patient surface and said x-ray source from a first sensor attached to said x-ray source bracket and receptor position data indicative of a distance between said receptor and a patient surface from a second sensor attached to said receptor bracket, said mainframe moving said x-ray source and receptor radially relative to said central axis based on said x-ray source and receptor position data.

8. The medical diagnostic imaging system of claim 1, further comprising a tracking subsystem receiving coordinate data representative of a patient surface from at least one sensor mounted on said receptor, said tracking subsystem setting a receptor radial distance relative to said central axis based on said coordinate data.

9. A method for acquiring multiple x-ray images utilized to reconstruct a three dimensional (3D) volume of patient information, the method comprising:

rotating an x-ray source and receptor about a central axis between at least first and second scan angles, said central axis corresponding to a region of interest in a patient;

radially moving at least one of the x-ray source and receptor to first radial distances from said central axis when at said first scan angle and radially moving the at least one of the x-ray source and receptor to second radial distances from said central axis when at said second scan angle, wherein a desired distance is maintained between said x-ray source and receptor at said first radial distances and paid second radial distances;

acquiring at least first and second images at said at least first and second scan angles; and constructing a three dimensional (3D) volumetric data set based on said at least first and second images.

10. The method of claim 9, the radially moving step further comprising defining a radial distance from said central axis to the receptor based on a radial distance from said central axis to a patient surface.

11. The method of claim 9, the radially moving step further comprising:

defining maximum and minimum radial distances relative to said central axis for the at least one of the x-ray source and receptor, and calculating intermediate radial distances corresponding to said at least first and second scan angles for the x-ray source and receptor based on said maximum and minimum radial distances.

12. The method of claim 9, the radially moving step further comprising detecting coordinate data comprising at least one of patient, receptor, and instrument coordinate information based on a distance between said central axis and one of a patient, said receptor, and an instrument, respectively, to define said first and second radial distances.

13. The method of claim 9, the radially moving step further comprising:

determining said first radial distance for the receptor relative to said central axis by radially moving the receptor towards a patient surface until receiving a sensor signal indicating a predefined distance between the receptor and the patient surface; and calculating said second radial distance for the x-ray source relative to said central axis based on said first radial distance for the receptor.

14. The method of claim 9, the radially moving step further comprising defining maximum and minimum radial distances relative to said central axis for the at least one of the x-ray source and receptor.

15. The method of claim 9, the radially moving step further comprising:

radially moving the receptor to said first radial distance relative to said central axis based on at least one of patient, receptor, and instrument coordinate information based on a distance between said central axis and one of a patient, said receptor, and an instrument, respectively; and radially moving the x-ray source to maintain a predetermined distance between the receptor and x-ray source.

16. An x-ray apparatus for acquiring x-ray images and reconstructing three dimensional (3D) volumes of patient information, comprising:
a C-arm unit having an x-ray source for generating x-rays and a receptor for obtaining image exposures from received x-rays, said C-arm unit moving said x-ray source and receptor along an image acquisition path between a series of exposure positions, said C-arm unit having a central axis corresponding to a region of interest in a patient, said C-arm unit rotating about said central axis;
x-ray source and receptor brackets mounting said x-ray source and receptor, respectively, to said C-arm unit, said x-ray source and receptor brackets moving at least one of said x-ray source and receptor in a radial direction toward and away from said central axis of the C-arm unit to maintain a desired distance between said x-ray source and receptor;
a data processor tracking component coordinate data based on at least one of a distance between said central axis and one of said receptor, said x-ray source, and a patient;
an image processor collecting a series of image exposures from said receptor obtained while said x-ray source and receptor are located at said series of exposure positions, said image processor receiving said component coordinate data from said data processor for said series of exposure positions corresponding to said series of image exposures and constructing a three dimensional (3D) volumetric data set based on said series of image exposures and said component coordinate data for said series of exposure positions; and
a display displaying images based on said (3D) volumetric data set.

17. The apparatus of claim 16, said receptor further comprising at least one sensor detecting a radial position of said receptor relative to a patient surface.

18. The apparatus of claim 16, further comprising:
a first sensor attached to said source bracket sending x-ray source coordinate data to said data processor, said x-ray source coordinate data indicative of a distance between said x-ray source and said central axis; and
a second sensor attached to said receptor bracket sending receptor coordinate data to said data processor, said receptor coordinate data indicative of a distance between said receptor and said central axis.

19. The apparatus of claim 16, further comprising a control panel for setting maximum and minimum radial distances relative to said central axis for at least one of said receptor and x-ray source.

20. The apparatus of claim 16, further comprising a sensor located proximate said receptor bracket for sensing position data of at least one of said receptor and a patient relative to said central axis, said x-ray source and receptor brackets radially moving said x-ray source and receptor, respectively, based on said position data.

21. The method of claim 1, wherein said desired distance comprises a uniform distance between said x-ray source and receptor.

22. The method of claim 1, wherein said desired distance maintains a region of interest of said patient at said central axis.

23. The method of claim 1, wherein said desired distance maintains a region of interest of said patient at an isocenter of said imaging system.

24. The method of claim 1, wherein a region of interest of said patient is maintained at said central axis for said series of image exposures.

25. A medical diagnostic imaging system, comprising:
a C-arm unit having an x-ray source for generating x-rays and a receptor for obtaining image exposures from received x-rays, said C-arm unit moving said x-ray source and receptor along an image acquisition path between at least first and second exposure positions, said C-arm unit rotating about a central axis corresponding to a region of interest in a patient;
x-ray source and receptor brackets mounting said x-ray source and receptor, respectively, to said C-arm unit, said x-ray source and receptor brackets moving said x-ray source and receptor to maintain said central axis for a series of image exposures;
an image processor collecting a series of image exposures from said receptor including at least first and second image exposures obtained while said x-ray source and receptor are located at said at least first and second exposure positions, respectively, said image processor collecting position data for multiple exposure positions corresponding to said series of image exposures, said image processor constructing a three dimensional (3D) volumetric data set based on said series of image exposures and said position data for said multiple exposure positions; and
a display displaying images based on said 3D volumetric data set.

26. The medical diagnostic imaging system of claim 25, further comprising a tracking subsystem receiving coordinate data comprising at least one of patient, receptor, and instrument coordinate information based on a distance between said central axis and one of a patient, said receptor, and an instrument, respectively, said x-ray source and receptor moving relative to said central axis based on said coordinate data while said x-ray source and receptor are located at said at least first and second exposure positions.

27. The medical diagnostic imaging system of claim 25, said receptor further comprising at least one sensor detecting a position of said receptor relative to a patient surface.

28. The medical diagnostic imaging system of claim 25, further comprising a tracking subsystem receiving coordinate data representative of a patient surface from at least one sensor mounted on said receptor, said tracking subsystem setting a receptor distance relative to said central axis based on said coordinate data.

29. A method for acquiring multiple x-ray images utilized to reconstruct a three dimensional (3D) volume of patient information, the method comprising:
rotating an x-ray source and receptor about a central axis between at least first and second scan angles, said central axis corresponding to a region of interest in a patient;
moving the x-ray source and receptor to first distances to maintain said central axis when at said first scan angle and moving the x-ray source and receptor to second distances to maintain said central axis when at said second scan angle;
acquiring at least first and second images at said at least first and second scan angles; and
constructing a three dimensional (3D) volumetric data set based on said at least first and second images.

30. The method of claim 29, the moving step further comprising detecting coordinate data comprising at least one of patient, receptor, and instrument coordinate information based on a distance between said central axis and one of a patient, said receptor, and an instrument, respectively, to define said first and second distances.

31. The method of claim 29, the moving step further comprising;

determining said first distance for the receptor relative to said central axis by moving the receptor towards a patient surface until receiving a sensor signal indicating a predefined distance between the receptor and the patient surface; and calculating said second distance for the x-ray source relative to said central axis based on said first distance for the receptor.

\* \* \* \* \*

UNITED STATES PATENT AND TRADEMARK OFFICE
CERTIFICATE OF CORRECTION

PATENT NO. : 6,814,489 B2
DATED : November 9, 2004
INVENTOR(S) : Jensen et al.

It is certified that error appears in the above-identified patent and that said Letters Patent is hereby corrected as shown below:

<u>Column 10,</u>
Line 20, delete "paid" and substitute therefore -- said --
Line 34, after the word "receptor" delete "," and substitute therefor -- ; --.

Signed and Sealed this

Fifteenth Day of March, 2005

JON W. DUDAS
*Director of the United States Patent and Trademark Office*